(12) United States Patent
Jen et al.

(10) Patent No.: US 7,080,556 B2
(45) Date of Patent: Jul. 25, 2006

(54) ULTRASONIC APPARATUS AND METHODS FOR THE MONITORING OF MELTING, MIXING AND CHEMICAL REACTION PROCESSES

(75) Inventors: Cheng-Kuei Jen, Brossard (CA); Zhigang Sun, Greenfield Park (CA); Jacques Tatibouet, Montreal (CA)

(73) Assignee: National Research Council of Canada, Ottawa (CA)

( * ) Notice: Subject to any disclaimer, the term of this patent is extended or adjusted under 35 U.S.C. 154(b) by 571 days.

(21) Appl. No.: 10/459,574

(22) Filed: Jun. 12, 2003

(65) Prior Publication Data

US 2004/0037742 A1 Feb. 26, 2004

Related U.S. Application Data

(60) Provisional application No. 60/388,379, filed on Jun. 14, 2002.

(51) Int. Cl.
*G01N 29/04* (2006.01)

(52) U.S. Cl. ............... 73/590; 73/61.46; 73/597

(58) Field of Classification Search ........... 73/590, 73/591, 593, 629, 861.27, 53.04, 54.02, 61.44, 73/61.46, 597
See application file for complete search history.

(56) References Cited

U.S. PATENT DOCUMENTS 5,060,507 A * 10/1991 Urmson et al. ............ 73/24.01
6,874,355 B1 * 4/2005 Kornfeldt et al. .......... 73/64.42
6,874,356 B1 * 4/2005 Kornfeldt et al. .......... 73/64.42
6,944,563 B1 * 9/2005 Melbø et al. ............... 702/100

* cited by examiner

*Primary Examiner*—Hezron Williams
*Assistant Examiner*—Jacques Saint-Surin
(74) *Attorney, Agent, or Firm*—G. Ronald Bell & Associates

(57) ABSTRACT

Ultrasonic apparatus and associated methods for the in-line monitoring of melting, mixing and chemical reaction processes of materials inside an enclosed chamber having rotating elements associated therewith are presented. The chamber may be heated and the rotating elements may be blades and/or screws. The chamber may be a heating barrel and the materials may be polymer and polymer composites pellets, metal pellets and chemical compounds. Ultrasonic sensors, which are preferably coupled to a wall of the chamber, may be high temperature ultrasonic transducers attached to the external surface of the chamber or ultrasonic buffer rods embedded into the chamber and coupled to cooled ultrasonic transducers. These sensors are operated in the reflection mode and are placed over the rotating elements. The number and locations of the sensors depend on applications. The synchronization of the transmission of the ultrasonic signals and the associated data acquisition with the position of the rotating element may be accomplished by using a high speed multiple-record data acquisition system. The ultrasonic speed and attenuation in the material being processed, or the traveling time in the material and the amplitude of the ultrasonic signals reflected by the rotating element, the ultrasonic reflection coefficient or the amplitude of the ultrasonic signals reflected at the chamber-material interface or the buffer rod probing end-material interface, and the ultrasonic signals scattered by the material within the chamber, can provide information on the melting, mixing and chemical reaction of the materials.

20 Claims, 7 Drawing Sheets

(a)

(b)

(c)

(a)

(b)

ULTRASONIC APPARATUS AND METHODS FOR THE MONITORING OF MELTING, MIXING AND CHEMICAL REACTION PROCESSES

CROSS REFERENCE TO RELATED APPLICATION

This application claims benefit of priority of provisional application Ser. No. 60/388,379 Provisional application titled "Ultrasonic Apparatus and Methods for the Monitoring of Melting, Mixing and Chemical Reaction Processes" filed on Jun. 14, 2002 whose inventors were Cheng-Kuei Jen, Zhigang Sun, and Jacques Tatibouet.

FIELD OF INVENTION

The present invention relates to an apparatus and associated methods for ultrasonic monitoring of industrial material processes, and more particularly to in-line ultrasonic monitoring of melting, mixing and chemical reaction of materials inside an enclosed chamber with rotating elements therein.

BACKGROUND OF THE INVENTION

Many industrial material fabrication processes involve melting, mixing and chemical reaction during material processing in an enclosed chamber. These processes are normally performed: at elevated temperature, which causes material to melt; with rotation elements, such as blades and/or screws, which provide the mixing mechanism. Materials can be polymers, polymer composites, metals, foods, or other materials in pellets, powder and liquid form. The chamber is normally made of metal such as steel, which is optically opaque.

Due to the complex geometry of the rotating elements and the complex properties and rheological behaviors of the materials encountered, the current understanding of the physics governing such melting, mixing and chemical reaction processes has remained insufficient. What hinders the understanding is the fact that operators could not see what was taking place in the chamber during melting, mixing and chemical reaction, especially when the feed material was changed from solid to the molten state. Direct viewing under active mixing actions is not convenient because the chambers are completely enclosed in metal and furthermore the rotation elements such as blades and screws are running. This is one of the main reasons that empirical approaches still dominate industrial melting, mixing and chemical reaction processes development and control.

In-line monitoring is an efficient way to overcome these difficulties. One would not only find out the state of the process, but also be able to use the data to correlate with the material properties such as the important product qualities. Conventional sensors such as temperature and pressure probes are normally used for such process monitoring; however, their response time is slow and the material properties cannot be directly monitored. The ultrasonic technique advantageously provides an ability to probe the interior of materials at elevated temperatures and pressures. It can be carried out non-destructively, non-invasively and in line.

However, because of the rotation and the odd shapes of the blades or screws which provide the necessary efficient melting, mixing and chemical reaction, synchronization between the ultrasonic measurement and the position of the rotating element, such as blades and/or screws, is required to track echo signals reflected from the rotating element in such a way that ultrasonic measurements can be done for nearly the same relative sensor-rotating element position.

Therefore, there is a need in industry for an improved ultrasonic apparatus and method for the monitoring of melting, mixing and chemical reaction processes.

SUMMARY OF THE INVENTION

The present invention, according to an aspect thereof, provides an apparatus for in-line monitoring of melting, mixing and chemical reaction of materials comprising: an enclosed chamber; at least one rotating element coupled to the chamber; a motor coupled to the at least one rotating element to provide a rotating force therefor; at least one ultrasonic sensor for measuring transmitted and received ultrasonic signals, said sensor bridging an interior and exterior of the enclosed chamber; and a position encoder coupled to the motor for providing synchronization between such ultrasonic measurement and a position of the at least one rotating element.

The ultrasonic apparatus operated in the reflection mode in which access to only one side of the chamber, such as a barrel, is required. To meet the requirement of synchronization between the ultrasonic measurement and the position of the rotating element, an optical encoder method and a multiple-record technique may be employed to track the position of the rotating element during each rotation.

According to an aspect of the present invention, there is provided an ultrasonic apparatus operated in the reflection mode for the monitoring of the melting, mixing and chemical reaction of materials in an enclosed chamber having rotating elements associated therewith. The rotating elements are rotated by a suitable means, such as a motor coupled to the rotating elements, to provide the necessary rotating force. Because of the rotation and the helical shapes of the rotating elements, such as screws, synchronization between the ultrasonic measurement and the screw position is required. Such synchronization can be achieved by using a position encoder. A preferred implementation of such position encoder is an optical encoder, which may be installed onto the axis of the motor, which provides the rotation force for the rotating element. For instance, a 12-bit optical encoder can provide an angular resolution of 0.1 degree. Furthermore, according to another embodiment of the present invention, a multiple-record technique may be advantageously employed. With this technique, it is possible to acquire hundreds of signals within one rotation period of the screw and easily achieve an angular resolution of 0.5 degree.

Thus, an aspect of the present invention provides an apparatus for in-line monitoring of melting, mixing and chemical reaction of materials comprising: an enclosed chamber; at least one rotating element coupled to the chamber; a motor coupled to the rotating element or elements to provide a rotating force therefore; an ultrasonic sensor for measuring transmitted and received ultrasonic signals; and a position encoder coupled to the motor for providing synchronization between such ultrasonic measurement and a position of the rotating element or elements.

An ultrasonic apparatus according to an aspect of the present invention comprises at least one ultrasonic sensor. Such ultrasonic sensors can be high temperature ultrasonic transducers (UTs) sitting on the outer surface of the chamber, with or without a high temperature couplant at the UT/chamber interface, buffer rods embedded in the chamber, or barrel, with a room temperature UT attached to the end outside the chamber, with an air or water cooling system, and a couplant at the UT/buffer rod interface, and buffer rods embedded in the chamber, or barrel, with a high temperature UT attached to the end outside the chamber, without any cooling system, and with or without a high temperature couplant at the UT/buffer rod interface.

Suppose the distance, D, between the internal surface of the chamber and the rotation element or between the probe end of the buffer rod sensor and the rotation element is known. One can measure the time of flight, $t_D$, between the ultrasonic echo reflected from the internal surface of the chamber, such as a barrel, and that reflected from the rotation element, such as blades and/or screws, or between the echo reflected from the end of the buffer rod sensor and that reflected from the rotational element. Then the ultrasonic velocity $c_P=2D/t_D$ of the material in the chamber can be calculated. The velocity and attenuation which can be deduced from the amplitudes of the reflected signals off the blade in the material are related to melting, mixing and chemical reaction status in the chamber. Furthermore the material in the chamber can affect the amplitude and time delay of the echo reflected from the buffer rod/material interface or chamber/material interface, which may be used to probe the material properties affected by the melting, mixing and chemical reaction processes.

Thus, an ultrasonic apparatus and associated methods for the in-line monitoring of melting, mixing and chemical reaction processes of materials inside an enclosed chamber having rotating elements associated therewith are presented. The chamber may be heated and the rotating elements may be blades and/or screws. The chamber may be a heating barrel and the materials can be polymers, polymer composites, metals, foods, or other materials in pellets, powder and liquid form. Ultrasonic sensors, which are preferably coupled to a wall of the chamber, may be high temperature ultrasonic transducers attached to the external surface of the chamber or ultrasonic buffer rods embedded into the chamber and coupled to cooled ultrasonic transducers. These sensors are operated in the reflection mode and are placed over the rotating elements. The number and locations of the sensors depend on applications. The synchronization of the transmission of the ultrasonic signals and the associated data acquisition with the position of the rotating element may be accomplished by using a high speed multiple-record data acquisition system. The ultrasonic speed and attenuation in the material being processed, or the traveling time in the material and the amplitude of the ultrasonic signals reflected by the rotating element, the ultrasonic reflection coefficient or the amplitude of the ultrasonic signals reflected at the chamber-material interface or the buffer rod probing end-material interface, and the ultrasonic signals scattered by the material within the chamber, can provide information on the melting, mixing and chemical reaction of the materials.

BRIEF DESCRIPTION OF THE DRAWINGS

For a more complete understanding of embodiments of the present invention and for further objects and advantages thereof, reference may be made to the following description taken in conjunction with the accompanying drawing in which.

DETAILED DESCRIPTION OF THE PREFERRED EMBODIMENTS OF THE INVENTION

Figure 1:
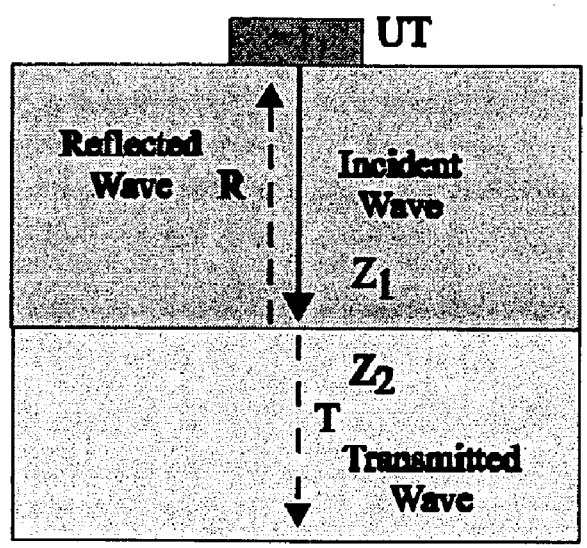
FIG. 1 is a schematic diagram of reflection and transmission of ultrasonic waves at an interface.

When ultrasonic waves impinge at the boundary between two different media as shown in FIG. 1, some of the energy is transmitted through the boundary and the rest is reflected back. The reflection and transmission coefficients, R and T, are respectively:

$$R = \frac{Z_1 - Z_2}{Z_1 + Z_2} \quad (1)$$

$$T = 1 - R \quad (2)$$

where $Z_i$ is the acoustic impedance of medium i, which is defined as the product of the mass density $\rho_i$ and the acoustic wave velocity $c_i$ of the material:

$$Z_i = \rho_i c_i (i=1,2) \quad (3)$$

Figure 2:
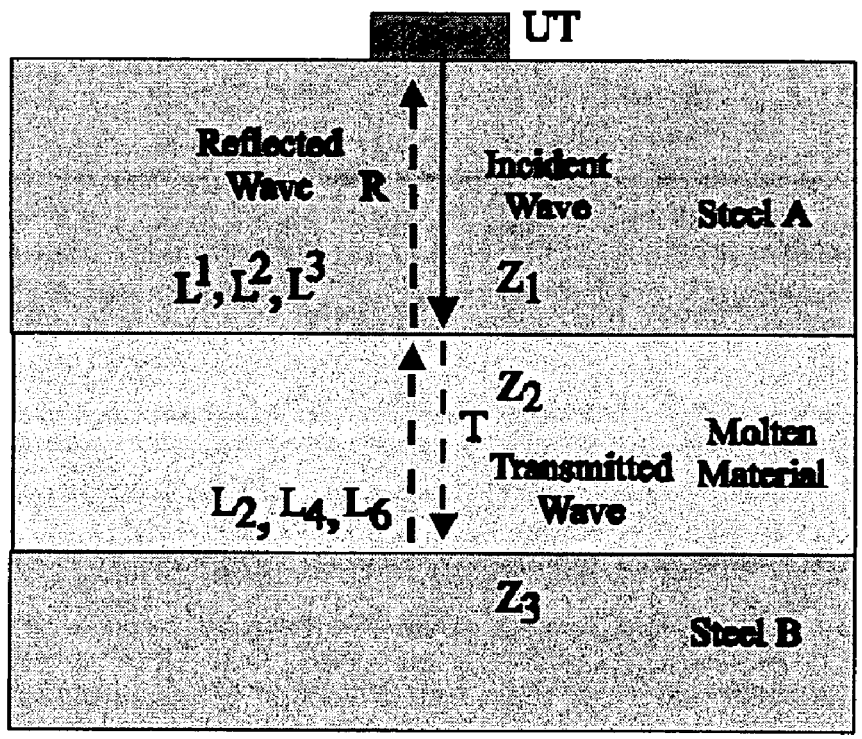
FIG. 2 is a schematic diagram of reflection and transmission of ultrasonic waves at two interfaces and the reverberation in the materials. Echoes $L^1$, $L^2$ and $L^3$ and $L_2$, $L_4$ and $L_6$ are the $1^{st}$, $2^{nd}$ and $3^{rd}$ round trip echoes in the steel A and material, respectively.

Ultrasonic measurements in the present invention preferably operate in the pulse-echo mode in which the signal is transmitted and received by the same ultrasonic transducer (UT). Only one-sided access to the processing machines is needed. In an embodiment of the present invention, three layers of materials are involved, as shown in FIG. 2. There are two interfaces. Let the materials in this example be: steel A type; molten material, such as a polymer; and steel B type. Because of the reverberation, there may exist echoes $L^1$, $L^2$ and $L^3$ and $L_2$, $L_4$ and $L_6$ which are the $1^{st}$, $2^{nd}$ and $3_{rd}$ round trip echoes in steel A and in the molten material, respectively. If the velocity, $c_A$, of the steel A type is known, the thickness, $h_A$, of the steel A type can be obtained as $h_A = c_A \times t_A/2$, where $t_A$ is the time delay between echoes $L^1$ and $L^2$ (or $L^2$ and $L^3$) and can be measured by using a cross-correlation method or other time delay measurement techniques. Similarly, if the thickness, $d_P$, is known, the velocity, $c_P$, of the molten material such as polymer can be obtained as $c_P = 2d_P/t_P$, where $t_p$ is the time delay between echoes $L_2$ and $L_4$ (or $L_4$ and $L_6$) and can be measured the same way $t_A$ is measured.

Figure 3:
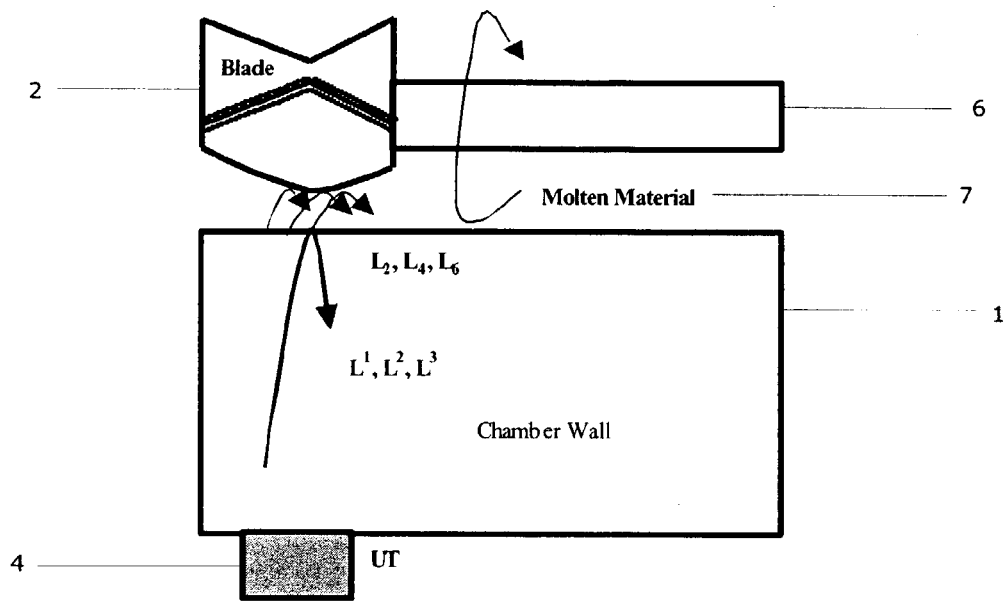
FIG. 3 depicts diagramatically ultrasonic echoes in the molten material reflected from the flight F and the root R of the screw, respectively. Echoes $L^1$, $L^2$ and $L^3$ and $L_2$, $L_4$ and $L_6$ are the $1^{st}$, $2^{nd}$ and $3^{rd}$ round trip echoes in the barrel wall and the material, respectively.

During an exemplary material manufacturing process, such as mixing of polymers, the three layers shown in FIG. 2 can be a Brabender mixer chamber made of one type of steel, a material and a blade made of another type of steel. The chamber may be heated and the blade may be the rotating element inside this chamber. During melting, mixing and chemical reaction, the blade is rotating. A blade (2), as shown in FIG. 3, is advantageously provided as a metal shaft (6) with an odd shape machined on the surface. It has a "Flight" F referring to the ridge (i.e. the outermost edge). Echoes $L_2$, $L_4$ and $L_6$ are the $1^{st}$, $2^{nd}$ and $3^{rd}$ round trip echoes, respectively, in the molten material (7) but reflected from the flight of the blade (2). From the ultrasonic travel time information between echoes $L^1$ and $L_2$ or that between $L_2$ and $L_4$ or between $L_4$ and $L_6$ and the distance $d_P$ between the inner chamber wall (1) and the flight of the blade (2), the velocity in the material, $C_M$, can be obtained. In order to determine the distance d accurately, there is a need to synchronize the ultrasonic measurement with the blade rotation, that is, to track the ultrasonic signals reflected from the same surface area of the rotating blade for each rotation during, for example, a melting and mixing process. In FIG. 3 an ultrasonic transducer (UT) (4) may be a high temperature piezoelectric sensor, which operates in the pulse-echo mode. Uts (4) may preferably be fixed onto the external surface of the chamber wall (1), e.g. brazed or glued thereon.

Figure 4:
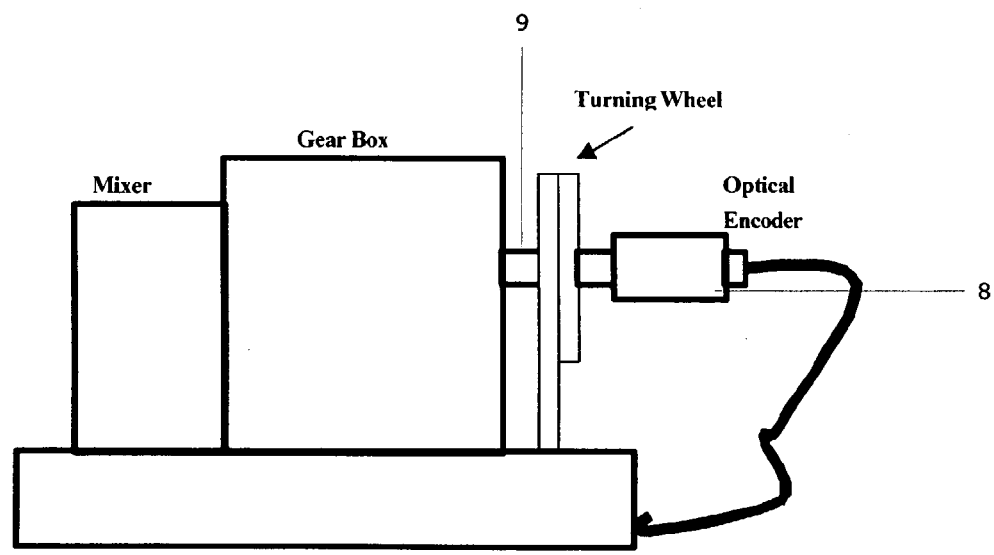
FIG. 4 shows diagramatically an optical encoder installed onto the axis of the motor which provides the rotation force for the rotating element for syncronizing ultrasonic measurement with screw rotation.

One technique to achieve synchronization of the ultrasonic pulses with the position of the rotating element for the in-line monitoring of melting, mixing and chemical reaction according to an embodiment of the present invention is to use a position encoder. Using this technique, during each rotation of the rotating element, such as a blade, this encoder sends a signal, which may be in electrical, optical or mechanical form, at specific rotation angles or locations of the rotating element to trigger the generation and acquisition of ultrasonic signals. In a preferred embodiment, an optical encoder (8) may be installed onto the axis (9) of the motor, which provides the rotation force for the rotating element as shown in FIG. 4. Using a 12-bit optical encoder, it is possible to achieve the synchronization of the transmission and acquisition of ultrasonic signals with an angular resolution of 0.09 degree with respect to the axis (9) of the motor as shown in FIG. 4. Higher angular resolution, which provides higher accuracy on the measurement of $C_M$, may be obtained if an optical encoder with higher than 12-bit resolution is used.

Figure 5:
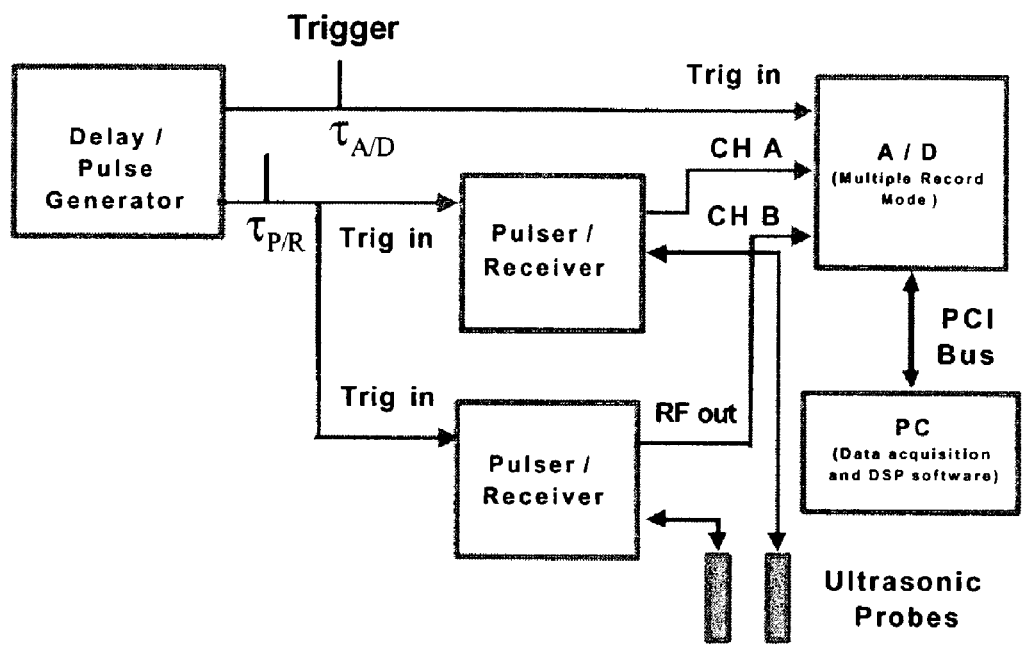
FIG. 5 is a schematic diagram of a multiple-record technique for synchronizing the ultrasonic measurement with the rotation of the rotating element, setup for monitoring at two locations.

Another method according to an embodiment of the present invention to achieve the desired synchronization is provided using a multiple-record method. This technique, as shown in FIG. 5, involves fast data acquisition by which it is possible to track the signals reflected from a given position of the rotating element, such as a blade, and then determine the distance d. This technique has been implemented on several PC-based data acquisition systems. With the use of a fast A/D board (a GAGE CS12100 card with 8 Megasample on board memory) and current ultrasonic equipment, it is possible to comfortably acquire up to 2000 signals within one second. At this acquisition speed, if the blade rotates at 200 rotations per minute (RPM), 600 signals per rotation will be present, which corresponds to an angular resolution of 0.6 degree. In many large production line screw extruders, the screw rotation speed is usually much less than 200 RPM. As a consequence, much better angular resolution can be achieved. Current data acquisition technology permits one to achieve an acquisition rate of 5,000 or even 10,000 ultrasound signals per second. For barrel and screw wear monitoring, the fastest data acquisition rate achievable is actually often determined by the thickness of the barrel (or the length of the ultrasonic probe). To avoid signals from overlapping, the time interval between two data acquisitions should preferably not be shorter than the time required for the multiple echoes generated inside the chamber to die out. Experimental results have demonstrated that the multiple-record technique can provide accurate position information during the rotation of a blade for the ultrasonic monitoring of melting, mixing and chemical reaction in a Brabender mixer chamber.

Figure 6:
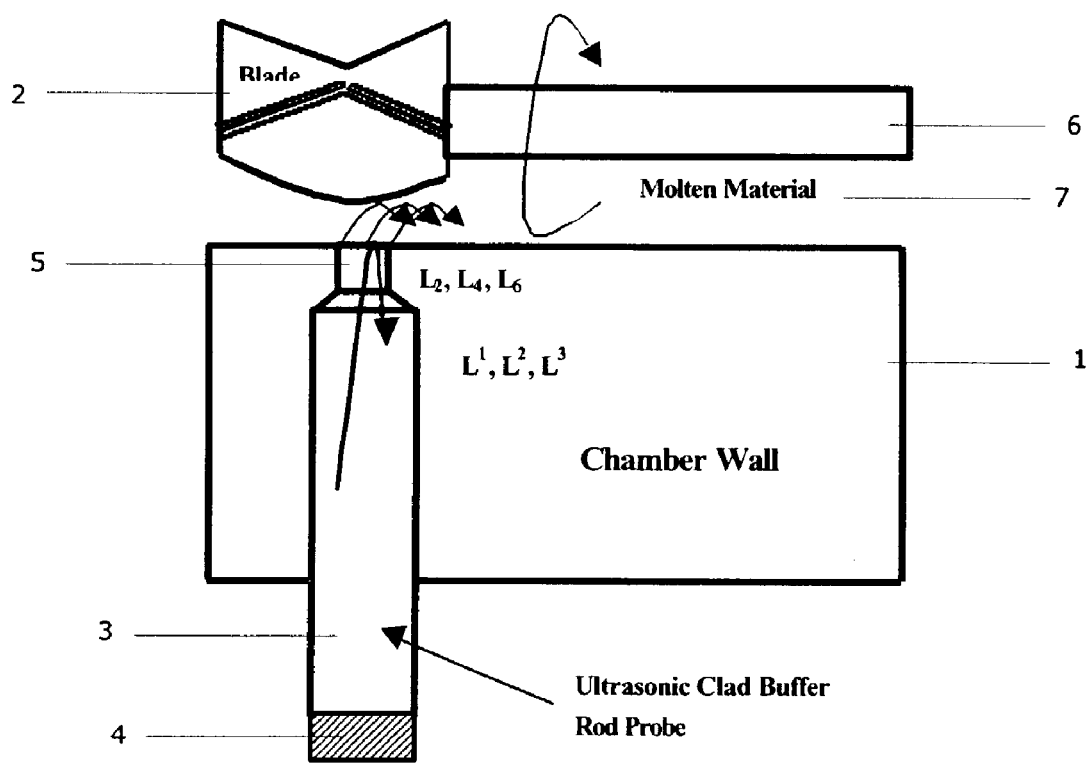
FIG. 6 illustrates ultrasonic clad buffer rod sensors required for measurement of melting, mixing and chemical reaction of the materials in the chamber, whereby echoes $L^1$, $L^2$ and $L^3$ are the $1^{st}$, $2^{nd}$ and $3^{rd}$ round trip echoes in the clad buffer rod, respectively.
Figure 7:
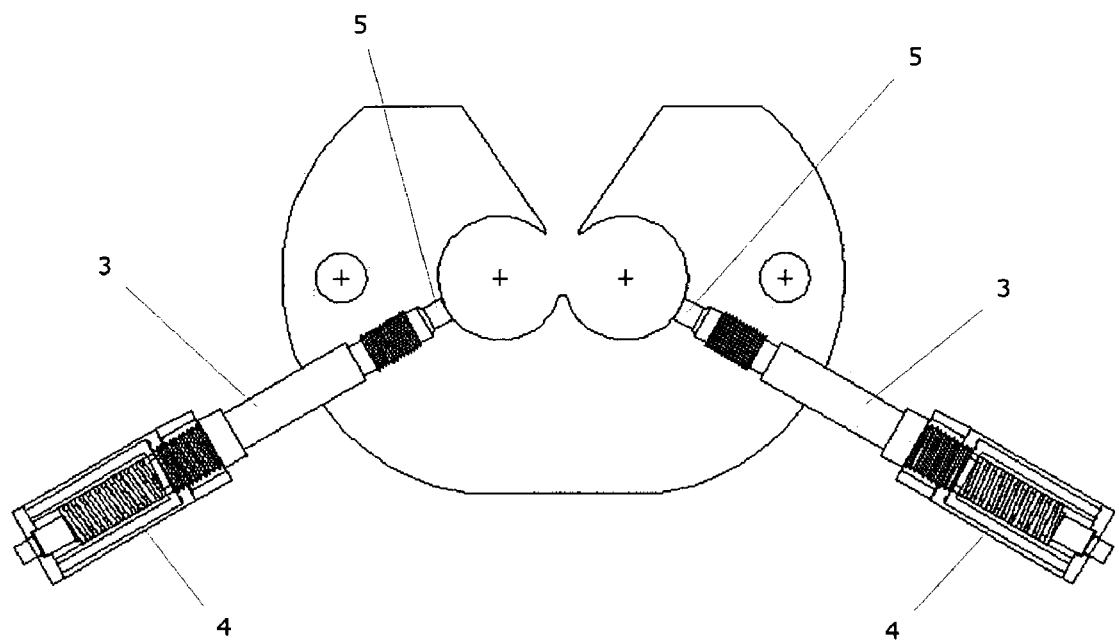
FIG. 7 shows two ultrasonic clad buffer rod sensors installed onto an internal mixer.

In addition to the sensor configuration shown in FIG. 3, FIG. 6 shows another sensor configuration according to an embodiment of the present invention in which a buffer rod (3) is advantageously embedded into the chamber wall (1). The probing end (5) of the buffer rod (3) is preferably flush with the inner cavity of the chamber in which the rotating element, such as a blade (2), is present. For example, FIG. 7 shows an exemplary experimental setup for in-line monitoring of melting, mixing and chemical reaction in a Brabender mixer. Two ultrasonic buffer rod sensors (3) are advantageously installed at the lower part of this mixer. The probing ends (5) of these two buffer rods (3) are preferably flush with the inner cavity of the mixer, as shown in FIG. 6. Both of these ultrasonic probes (3) are operated in the reflection mode. This means that the UT (4) located at the UT end (opposite of the probing end) of the buffer rod (3) serves as the transmitter as well as the receiver. Ultrasonic measurement data are advantageously recorded simultaneously with those of temperature and torque.

Figure 8:
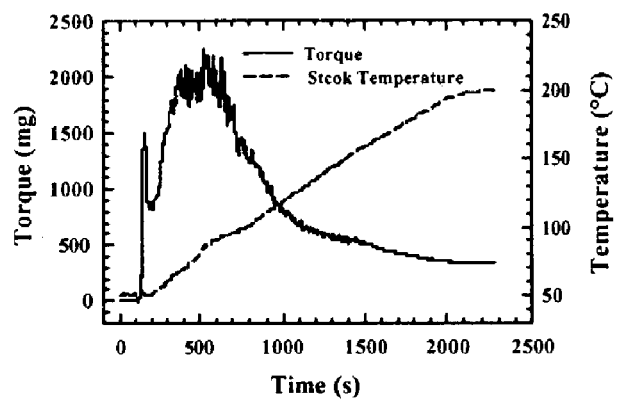
FIG. 8 illustrates graphically in-line monitoring of the melting of LDPE in the internal mixer (a) temperature and torque profile versus process time, (b) ultrasonic signal amplitude profile of $L_2$ versus process time and (c) ultrasonic signal amplitude profile of $L_2$ versus temperature.
Figure 8:
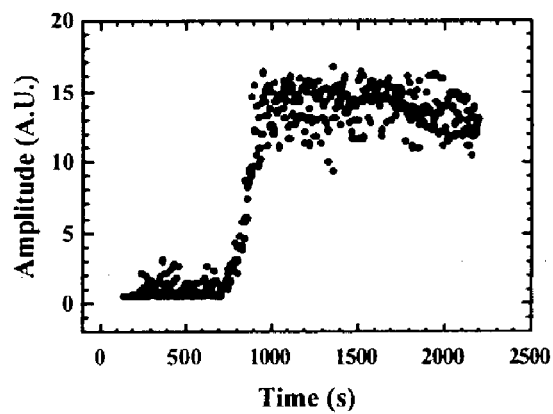
Figure 8:
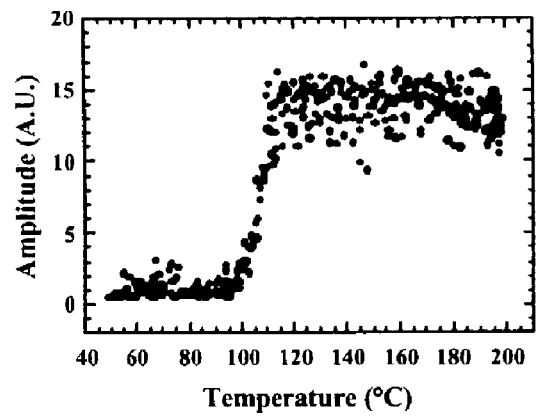

FIGS. 8(*a*), 8(*b*) and 8(*c*) present exemplary data for in-line monitoring of the melting of low density polyethylene (LDPE) in a Brabender mixer. A temperature and torque profile versus process time, ultrasonic signal amplitude profile of $L_2$ versus process time, and ultrasonic signal amplitude profile of $L_2$ versus temperature are shown in FIGS. 8(*a*), 8(*b*) and 8(*c*), respectively. $L_2$ is the ultrasonic signal having exited from the probing end of the buffer rod, entered into the LDPE being melted and reflected from the flight of the rotating blade. It is evident, from the ultrasonic monitoring data presented in FIG. 8(*c*), that the LDPE starts to melt at around 100° C. and reaches complete melt stage at around 120° C. Such information cannot be obtained from the torque measurement data as shown in FIG. 8(*a*).

Figure 9:
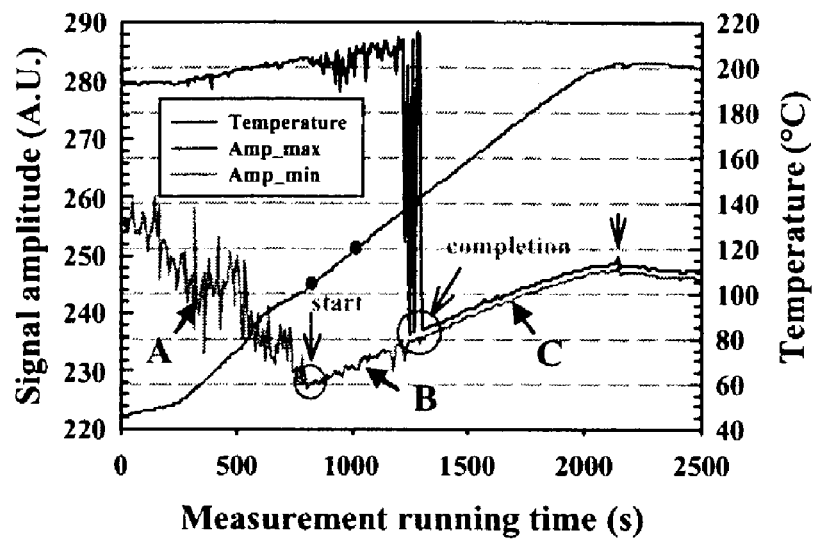
FIG. 9 is a graph showing ultrasonic in-line monitoring of the melting of LDPE in the internal mixer together with temperature measurement, whereby ultrasonic signal amplitude profile of the probe/material interface echo $L^5$ is used.

FIG. 9 shows another ultrasonic method according to an embodiment of the present invention for monitoring the melting of a material, such as solid pellets of LDPE. In this figure, the amplitude variation of the echo $L^5$ at the probe end/material interface is used. $L^5$ is the $5^{th}$ round trip echo in the buffer rod. Generally speaking, within the acceptable signal-to-noise ratio range, the larger the number of round trips, the better the sensitivity of the echo to the degree of melting. In this figure, Amp_max and Amp_min are the upper and lower limits of the variation of the amplitude of $L^5$ during each rotation of the rotating element. The region A indicates that the solid pellets of LDPE are being softened. The point indicated by the label 'start' may be considered as the start of the melting. The point indicated by the label 'completion' may be regarded as the completion point of the melting.

Figure 10:
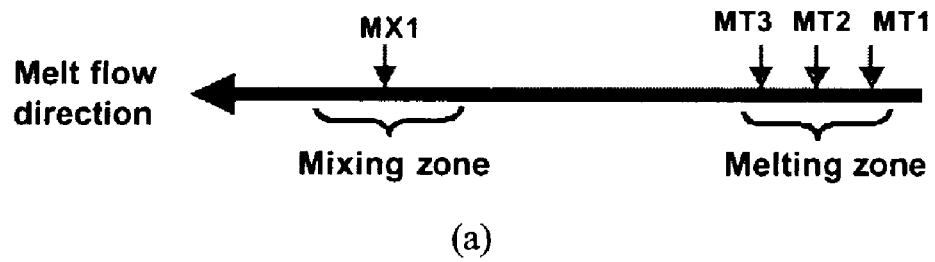
FIG. 10 illustrates ultrasonic in-line monitoring of the mixing of 99% LDPE and 1% $CaCO_3$ powder in a twin-screw extruder with (a) being a schematic diagram and (b) a chart monitoring results, whereby the lower the signal fluctuation coefficient β of echo signal $L_2$, the better is the mixing.
Figure 10:
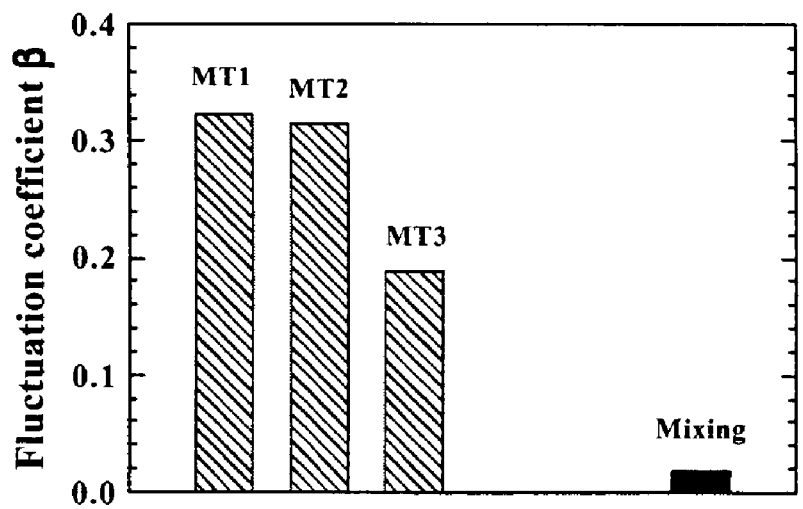

FIG. 10 presents experimental data of in-line ultrasonic monitoring of the mixing of 99% LDPE and 1% $CaCO_3$ in a W&P 30 mm twin-screw extruder according to an embodiment of the present invention. In this case, three buffer sensors are installed at positions MT1, MT2 and MT3 in the melting zone and one is installed at position MX1 in the mixing zone for the monitoring of the mixing of 99% LDPE and 1% $CaCO_3$ powder. The fluctuation of the amplitude of echo $L_2$ gradually reduces during the mixing. This coefficient, $L_2$, is an evaluation of how well the mixing has been achieved. The lower is the signal fluctuation coefficient β of $L_2$ (defined as the ratio of the standard deviation of signal amplitude over the average value of the later), the better is the mixing.

Figure 11:
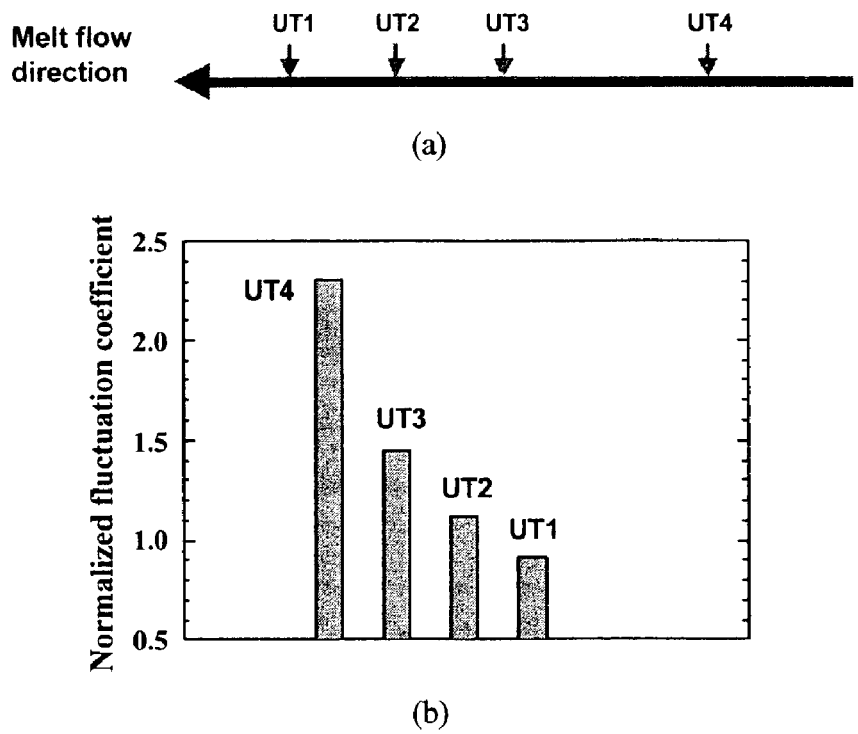
FIG. 11 illustrates ultrasonic in-line monitoring of the mixing of 98% HDPE and 2% PS in a single-screw extruder with (a) being a schematic diagram and (b) a chart monitoring results, whereby, the lower the normalized signal fluctuation coefficient of echo signal $L_2$, the better is the mixing.

FIG. 11 presents experimental data of in-line ultrasonic monitoring of the mixing of 98% high density polyethylene (HDPE) and 2% polystyrene (PS) in a FLAG single-screw extruder according to an embodiment of the present invention. In this case, four buffer sensors are installed at 4 locations indicated in FIG. 11(a). The normalized fluctuation coefficient of the amplitude of echo $L_2$ (defined as the ratio of the signal fluctuation coefficient β of the polymer blend to that of the matrix material HDPE) gradually reduces. This coefficient, $L_2$, is an evaluation of how well the mixing has been achieved. The lower is the normalized signal fluctuation coefficient of $L_2$, the better is the mixing.

Figure 12:
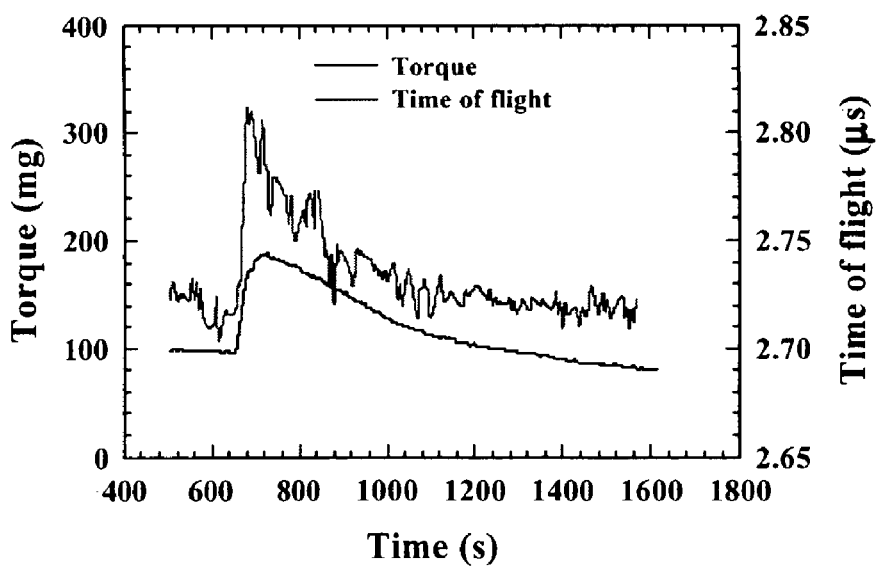
FIG. 12 illustrates graphically ultrasonic in-line monitoring of reactive mixing of 40 g PPgMAH and 0.3 g Jeffamine in the internal mixer.

FIG. 12 shows experimental data of in-line monitoring of the chemical reaction during reactive mixing of 40 g PPg-MAH and 0.3 g Jeffamine in the Brabender mixer according to an embodiment of the present invention. It can be seen that during the chemical reaction, the torque changes due to the variation of the viscosity of the material in the mixer. However, ultrasonic speed in the material also changes for the same reason. In FIG. 12, the variation of the time of flight of the ultrasonic echo L2 follows well that of the torque measurement.

In summary, the above description outlines embodiments of the present invention that provide an apparatus for ultrasonic monitoring of melting, mixing and chemical reaction using an encoder as shown in FIG. 4, and a method of ultrasonic monitoring of melting, mixing and chemical reaction using multiple recording technique as shown in FIG. 5. Embodiments of the present invention have also been described relating to an ultrasonic sensor arrangement as illustrated in FIG. 2 and FIG. 6, and to ultrasonic monitoring methods of the melting, mixing and chemical reaction as shown in FIGS. 8–12.

The invention claimed is:

1. An apparatus for in-line monitoring of melting, mixing and chemical reaction of materials comprising:
   an enclosed chamber;
   at least one rotating element coupled to the chamber;
   a motor coupled to the at least one rotating element to provide a rotating force therefor;
   at least one ultrasonic sensor for measuring transmitted and received ultrasonic signals, said sensor bridging an interior and exterior of the enclosed chamber; and
   a position encoder coupled to the motor for providing synchronization between such ultrasonic measurement and a position of the at least one rotating element.

2. An apparatus for in-line monitoring of melting, mixing and chemical reaction of materials according to claim 1, wherein said at least one rotating element is a blade.

3. An apparatus for in-line monitoring of melting, mixing and chemical reaction of materials according to claim 1, wherein said at least one rotating element is a screw.

4. An apparatus for in-line monitoring of melting, mixing and chemical reaction of materials according to claim 1, wherein said position encoder is an optical encoder.

5. An apparatus for in-line monitoring of melting, mixing and chemical reaction of materials according to claim 1, wherein said position encoder further comprises a high speed multiple-record data acquisition system.

6. An apparatus for in-line monitoring of melting, mixing and chemical reaction of materials according to claim 1, wherein said at least one ultrasonic sensor is a high temperature ultrasonic transducer positioned on an outer surface of the chamber.

7. An apparatus for in-line monitoring of melting, mixing and chemical reaction of materials according to claim 6, further comprising a high temperature couplant at an interface between the high temperature ultrasonic transducer and the chamber.

8. An apparatus for in-line monitoring of melting, mixing and chemical reaction of materials according to claim 1, wherein said at least one ultrasonic sensor is a buffer rod embedded in the chamber with a room temperature ultrasonic transducer attached to the end of the buffer rod outside the chamber, and wherein said buffer rod includes a cooling system and a couplant at the interface between the ultrasonic transducer and the buffer rod.

9. An apparatus for in-line monitoring of melting, mixing and chemical reaction of materials according to claim 1, wherein said at least one ultrasonic sensor is a buffer rod embedded in the chamber with a high temperature ultrasonic transducer attached to an end of the buffer rod outside the chamber.

10. An apparatus for in-line monitoring of melting, mixing and chemical reaction of materials according to claim 9, further comprising a high temperature couplant at the interface between the ultrasonic transducer and the buffer rod.

11. A method for in-line monitoring of melting, mixing and chemical reaction of materials using an apparatus according to claim 1, wherein a value is measured representing a time required for an ultrasonic signal to travel from the ultrasonic sensor to an internal surface of the chamber and return to the sensor, wherein said value is then used to calculate an ultrasonic velocity of the material in the chamber, said ultrasonic velocity being related to the melting, mixing and chemical reaction status in the chamber.

12. A method for in-line monitoring of melting, mixing and chemical reaction of materials using an apparatus according to claim 1, wherein attenuations of reflected signals are calculated from amplitudes of the reflected signals, said attenuations being proportional to melting, mixing and chemical reaction status in the chamber.

13. A method for in-line monitoring of melting, mixing and chemical reaction of materials using an apparatus according to claim 1, wherein a scattering of ultrasonic signals effect brought about by materials in the chamber is proportional to melting, mixing and chemical reaction status in the chamber.

14. A method for in-line monitoring of melting, mixing and chemical reaction of materials according to claim 11, wherein measurements are taken at an interface between the chamber and the materials within the chamber.

15. A method for in-line monitoring of melting, mixing and chemical reaction of materials according to claim 12, wherein measurements are taken at an interface between the chamber and the materials within the chamber.

16. A method for in-line monitoring of melting, mixing and chemical reaction of materials according to claim 13, wherein measurements are taken at an interface between the chamber and the materials within the chamber.

17. A method for in-line monitoring of melting, mixing and chemical reaction of materials according to claim 11, wherein measurements are taken at an interface between the interior end of the ultrasonic sensor and the materials within the chamber.

18. A method for in-line monitoring of melting, mixing and chemical reaction of materials according to claim 12, wherein measurements are taken at an interface between the interior end of the ultrasonic sensor and the materials within the chamber.

19. A method for in-line monitoring of melting, mixing and chemical reaction of materials according to claim 13, wherein measurements are taken at an interface between the interior end of the ultrasonic sensor and the materials within the chamber.

20. A method for in-line monitoring of melting, mixing, and chemical reaction of materials using an apparatus according to claim 1, wherein an ultrasonic wave is transmitted into materials disposed within the enclosed chamber and at least one of melting, mixing, or chemical reaction status within the chamber is determined by measuring at least one of transmission velocity of said ultrasonic wave, attenuation of said ultrasonic wave, or a scattering effect of said ultrasonic wave.

\* \* \* \* \*